(12) United States Patent
Burles et al.

(10) Patent No.: US 8,241,574 B2
(45) Date of Patent: Aug. 14, 2012

(54) OPHTHALMIC DEVICE COMPRISING A HOLOGRAPHIC SENSOR

(75) Inventors: Barry Burles, Cambs (GB); Roger Bradley Millington, Huntingdon (GB); Christopher Robin Lowe, Cambridge (GB); Satyamoorthy Kabilan, Cambridge (GB); Jeffrey Blyth, Cambridge (GB)

(73) Assignee: Smart Holograms Limited, Cambridge (GB)

( * ) Notice: Subject to any disclaimer, the term of this patent is extended or adjusted under 35 U.S.C. 154(b) by 0 days.

(21) Appl. No.: 13/192,992

(22) Filed: Jul. 28, 2011

(65) Prior Publication Data

US 2011/0286064 A1 Nov. 24, 2011

Related U.S. Application Data

(63) Continuation of application No. 12/032,650, filed on Feb. 16, 2008, now Pat. No. 7,998,412, which is a continuation-in-part of application No. 10/169,502, filed as application No. PCT/GB01/00061 on Jan. 8, 2001, now abandoned, application No. 13/192,992, which is a continuation-in-part of application No. 10/573,097, filed as application No. PCT/GB2004/004093 on Sep. 27, 2004, now abandoned.

(30) Foreign Application Priority Data

Jan. 20, 2000 (GB) .................................. 0000209.7
Sep. 25, 2003 (GB) .................................. 0322488.8
Jan. 22, 2004 (GB) .................................. 0401399.1

(51) Int. Cl.
*G01N 15/06* (2006.01)
*G01N 33/00* (2006.01)
*G01N 33/48* (2006.01)

(52) U.S. Cl. ......... 422/82.05; 422/55; 422/56; 436/528; 436/529; 436/530; 436/531; 436/164; 436/165; 436/169; 600/300; 600/318; 600/319; 600/316

(58) Field of Classification Search ................... 422/55, 422/56, 82.05; 436/528, 529, 530, 531, 164, 436/165, 169; 600/300, 318, 319, 316
See application file for complete search history.

(56) References Cited

U.S. PATENT DOCUMENTS

| | | | |
|---|---|---|---|
| 3,917,453 A | 11/1975 | Milligan et al. | |
| 3,958,560 A * | 5/1976 | March | 600/319 |
| 4,059,407 A | 11/1977 | Hochstrasser | |
| 4,509,818 A | 4/1985 | Prikryl | |

(Continued)

FOREIGN PATENT DOCUMENTS

EP  A-0655470  5/1995

(Continued)

OTHER PUBLICATIONS

Kikuchi, A. et al., "Glucose-Sensing Electrode Coated With Polymer Complex Gel Containing Phenylboronic Acid," *Analytical Chemistry*, 1996, vol. 68, No. 5, pp. 823-828.

(Continued)

*Primary Examiner* — Brian J Sines
(74) *Attorney, Agent, or Firm* — Saliwanchik, Lloyd & Eisenschenk

(57) ABSTRACT

An ophthalmic device which comprises a holographic element comprising a medium comprising a phenylboronic acid group and, disposed therein, a hologram, wherein an optical characteristic of the element changes as a result of a variation of a physical property of the medium, and wherein the variation arises as a result of interaction between the medium and an analyte present in an ocular fluid.

13 Claims, 11 Drawing Sheets

U.S. PATENT DOCUMENTS

| | | | |
|---|---|---|---|
| 4,641,934 A * | 2/1987 | Freeman | 351/159 |
| 4,642,112 A * | 2/1987 | Freeman | 623/6.3 |
| 4,655,565 A * | 4/1987 | Freeman | 351/159 |
| 4,788,115 A | 11/1988 | Long et al. | |
| 5,103,325 A | 4/1992 | Andrews et al. | |
| 5,242,828 A | 9/1993 | Bergström et al. | |
| 5,401,667 A | 3/1995 | Koike | |
| 5,436,161 A | 7/1995 | Bergström et al. | |
| 5,514,501 A | 5/1996 | Tarlov | |
| 5,571,401 A | 11/1996 | Lewis et al. | |
| 5,583,163 A | 12/1996 | Müller | |
| 5,611,998 A | 3/1997 | Aussenegg et al. | |
| 5,665,840 A | 9/1997 | Pöhlmann et al. | |
| 5,712,356 A | 1/1998 | Bothe et al. | |
| 5,734,485 A | 3/1998 | Buchkremer et al. | |
| 5,849,841 A | 12/1998 | Mühlebach et al. | |
| 5,989,923 A | 11/1999 | Lowe et al. | |
| 6,139,145 A * | 10/2000 | Israel | 351/160 R |
| 6,165,408 A | 12/2000 | Steinmann | |
| 6,277,330 B1 | 8/2001 | Liu et al. | |
| 6,303,687 B1 | 10/2001 | Müller | |
| 6,366,369 B2 * | 4/2002 | Ichikawa et al. | 359/12 |
| 6,479,587 B1 | 11/2002 | Stockinger et al. | |
| 6,579,673 B2 | 6/2003 | Everhart et al. | |
| 6,689,316 B1 * | 2/2004 | Blyth et al. | 422/400 |
| 7,048,378 B2 * | 5/2006 | Chen | 351/177 |
| 7,181,121 B2 * | 2/2007 | Kuramoto et al. | 385/132 |
| 2001/0055754 A1 | 12/2001 | McGrath et al. | |
| 2003/0027240 A1 * | 2/2003 | Asher et al. | 435/25 |
| 2003/0035917 A1 | 2/2003 | Hyman | |
| 2003/0103868 A1 | 6/2003 | Millington | |
| 2005/0008317 A1 * | 1/2005 | Kuramoto et al. | 385/129 |
| 2007/0002470 A1 | 1/2007 | Domschke et al. | |

FOREIGN PATENT DOCUMENTS

| | | |
|---|---|---|
| EP | A-0712867 | 5/1996 |
| EP | A-0932635 | 8/1999 |
| EP | A-0958315 | 11/1999 |
| EP | A-0961941 | 12/1999 |
| JP | 2002-500381 | 1/2002 |
| JP | 2003-507717 | 2/2003 |
| WO | WO 95/26499 | 10/1995 |
| WO | WO 98/10334 | 3/1998 |
| WO | WO 98/43086 | 10/1998 |
| WO | WO 99/34239 | 7/1999 |
| WO | WO 99/34244 | 7/1999 |
| WO | WO 99/34248 | 7/1999 |
| WO | WO 99/63408 | 12/1999 |
| WO | WO-A-00/31150 | 6/2000 |
| WO | WO 02/054137 | 7/2002 |
| WO | WO 03/087789 | 10/2003 |
| WO | WO 03/087899 | 10/2003 |
| WO | WO 2004/081624 | 9/2004 |
| WO | WO 2005/015184 | 2/2005 |

OTHER PUBLICATIONS

Marshall et al. "Analyte-responsive holograms for (bio)chemical analysis" *J. Phys.:Condens. Matter*, 2006, pp. S619-S626, vol. 18.

Mayes et al. "A holographic sensor based on a rationally designed synthetic polymer" *J. Molecular Recognition*, 1998, pp. 168-174, vol. 11.

* cited by examiner

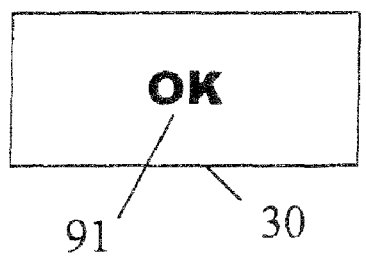 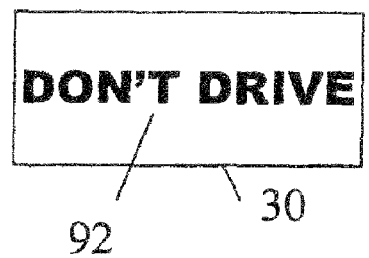
Fig. 9a    Fig. 9b
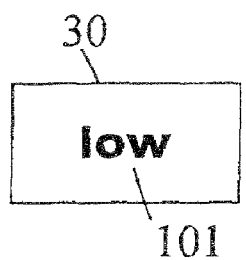 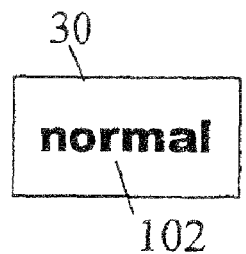 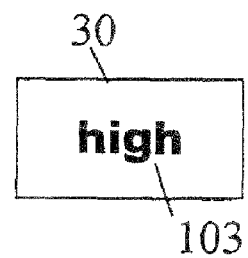
Fig. 10a    Fig. 10b    Fig. 10c

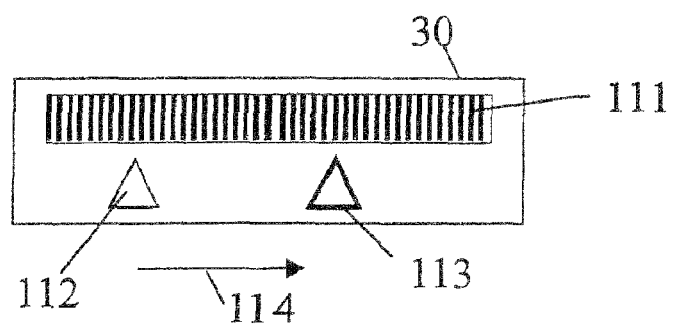
Fig. 11
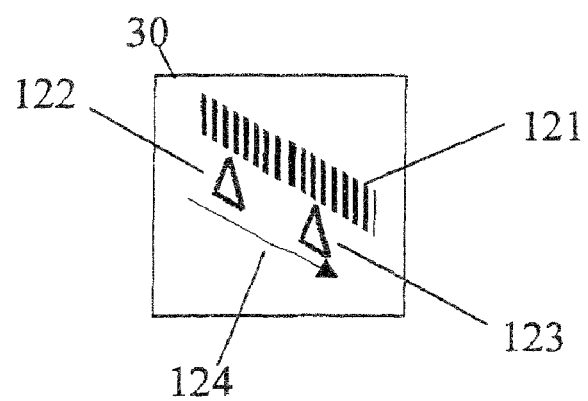
Fig. 12
Fig. 13
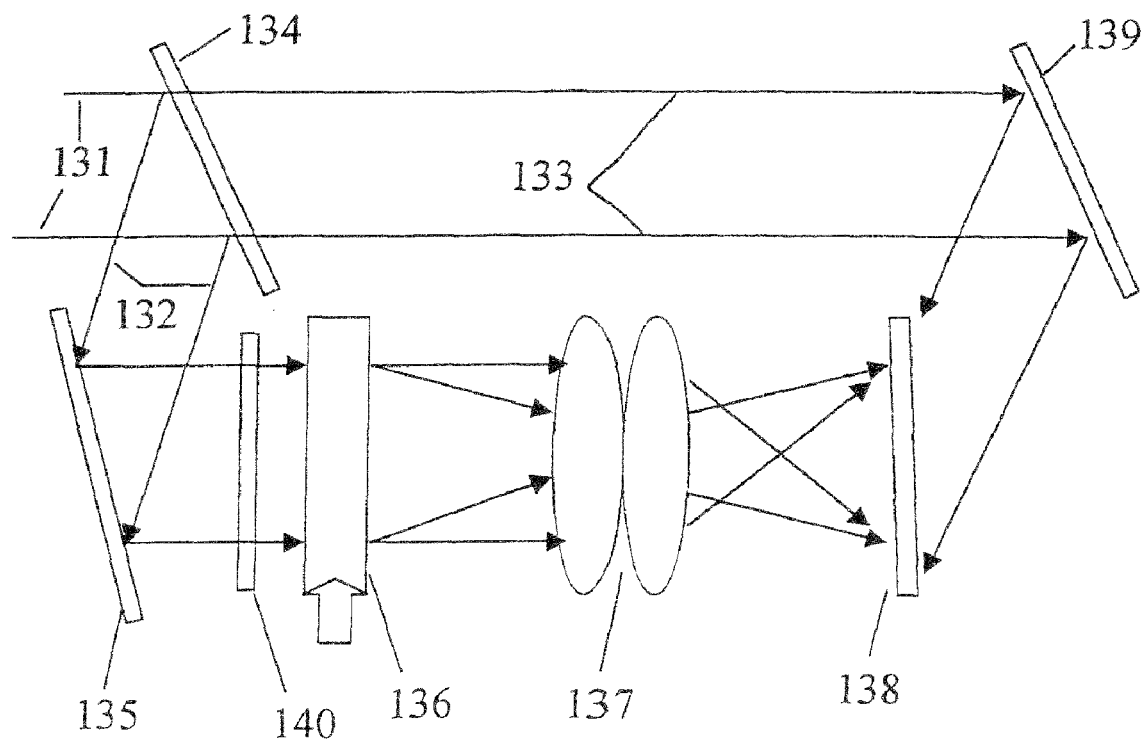

OPHTHALMIC DEVICE COMPRISING A HOLOGRAPHIC SENSOR

REFERENCE TO RELATED APPLICATIONS

This application is a continuation application of Application Ser. No. 12/032,650, filed Feb. 16, 2008, now U.S. Pat. No. 7,998,412, issued Aug. 16, 2011; which is a continuation-in-part of Application Ser. No. 10/169,502, filed Jul. 23, 2002 now abandoned; which is a national phase application of International Application No PCT/GB2001/00061, filed Jan. 8, 2001; which claims priority to Great Britain Application No 0000209.7, filed Jan. 7, 2000. This application is also a continuation-in-part of Application Ser. No. 10/573,097, filed Mar. 23, 2006 now abandoned; which is a national phase application of International Application No PCT/GB2004/004093, filed Sep. 27, 2004; which claims priority to Great Britain Application Nos. 0401399.1, filed Jan. 22, 2004 and 0322488.8, filed Sep. 25, 2003; and all of which are incorporated herein in their entirety.

FIELD OF THE INVENTION

The present invention relates generally to sensors and more particularly to an ophthalmic device such as a contact lens comprising a holographic, e.g. multiplexed, sensor.

BACKGROUND OF THE INVENTION

Ophthalmic devices, for example contact lenses, comprising holographic elements are known. Typically, a holographic element is used to focus incoming light. The holographic element may have a programmed activating angle providing two or more optical powers. The use of a holographic element allows the user to see clear and unimpaired images, thereby overcoming many of the shortfalls of traditional simultaneous vision and translating lenses. Holographic optical inserts are described, for example, in WO99/34239, WO99/34244, WO02/054137 and WO99/34248.

Chemical sensors and biosensors in the form of volume holograms made in specially made polymer layers are known. WO95/26499 discloses a sensor which comprises a reflection hologram made in a thin film of polymeric material where the polymer interacts with a substance to be detected so as to alter the optical properties of the hologram, thereby providing a means for detecting or quantifying that substance. More generally, this reference and also WO99/64308 disclose the concept of a volume hologram sensor which provides a measurable or observable optical change.

Within the art of holography, multiple holographic images and methods for creating them in a single holographic recording material are known. U.S. Pat. No. 4,509,818 discloses a method of making a three-dimensional holographic multiplexed image from a series of two-dimensional images. U.S. Pat. No. 5,103,325 discloses a method of holographically recording a series of two-dimensional images such that the viewed holographic images are observed separately and distinctly from each other. U.S. Pat. No. 5,734,485 discloses a method of producing three-dimensional still or moving scene holograms including recordings of computer-generated scenes.

These known systems produce sets of holographic images which are multiplexed in a degree-of-freedom which is only spatial, where the images are intended to be viewable by an observer as an artificially-produced three-dimensional image or as a set of images separated in space over a corresponding set of angles of view. The optical properties of the material in which these holograms are made are intended to be invariant in time and they are not intended to be altered chemically when functioning normally.

SUMMARY OF THE INVENTION

The present invention is based on the realisation that holographic sensing technology, when incorporated into a contact lens or other ophthalmic device, provides an accurate yet minimally invasive method of detection of an ocular analyte. Such sensing technology may allow for the continuous, real-time sensing of glucose or other carbohydrates. The invention thus may improve the lives of patients having diabetes and decrease such patients' risk of developing hypoglycemia or hyperglycemia.

One aspect of the invention is a contact lens including a volume hologram sensor which provides a measurable or observable optical change responsive to an ambient substance to be monitored or detected.

Another aspect of this invention is an ophthalmic device which comprises a holographic element comprising a medium and, disposed therein, a hologram, wherein an optical characteristic of the element changes as a result of a variation of a physical property of the medium, and wherein the variation arises as a result of interaction between the medium and an analyte present in an ocular fluid. The device may be a contact lens or an ocular implant.

Yet another aspect of the invention is a method of detection of an analyte in an ocular fluid, the method comprising detecting any change of the optical characteristic of the holographic element of a device of the invention with the fluid, in the eye.

A further aspect of the invention is a method for the production of a device of the invention which comprises contacting the holographic element with a contact lens, wherein the contacted regions of the element and the lens are cross-linkable; and cross-linking said regions.

The invention may be used for the detection of ocular analytes such as glucose or lactate. The interaction is preferably reversible so that both the interaction and reverse interaction can occur, allowing the analyte to be continuously detected, preferably in real time. The interaction is preferably a chemical reaction.

BRIEF DESCRIPTION OF THE DRAWINGS

FIGS. 9a and 9b are each schematic representations of a holographic sensor illustrating changing images in the form of messages relating to the application of the sensor.

FIGS. 10a to 10c are each schematic representations of a holographic sensor illustrating changing images in the form of messages relating to the amount of substance or substances being detected.

FIG. 11 is a schematic representation of a holographic sensor illustrating a changing image in the form of a moving indicator against a fixed scale.

FIG. 12 is a schematic representation of a holographic sensor illustrating a changing image in the form of an indicator moving in the depth of the image against an image of a scale located in the depth of the image.

FIG. 13 is a schematic of an optical layout which can be used to expose a photosensitive holographic film or plate to multiple images with the purpose of making a wavelength-multiplexed holographic sensor.

FIG. 21b is a side view of the holographic element taken along line A-A' of FIG. 21a.

DESCRIPTION OF PREFERRED EMBODIMENTS

Figure 1:
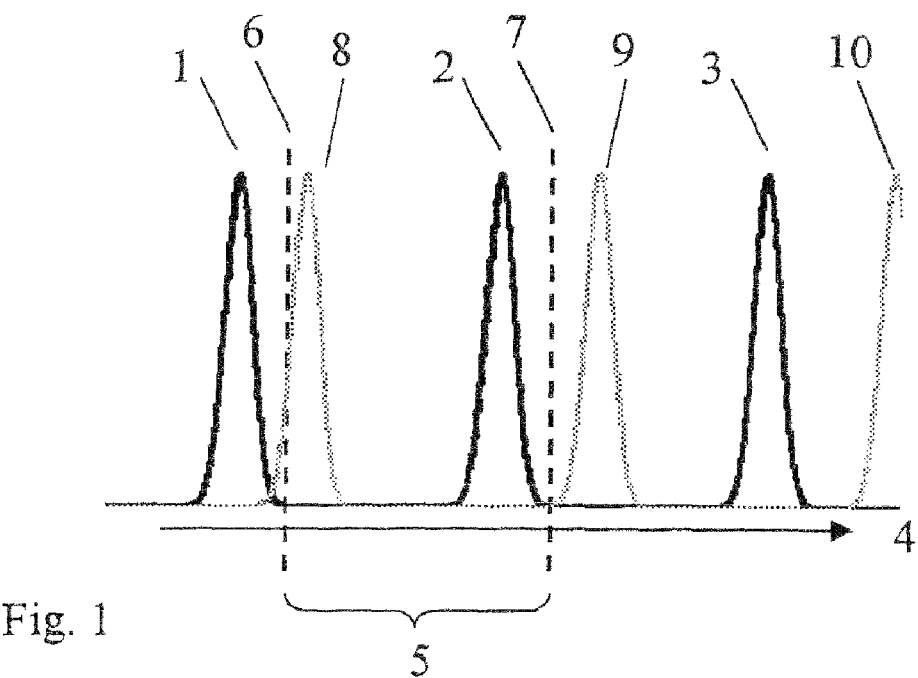
FIG. 1 shows an example of the multiple spectral peaks of a multiplexed reflection hologram, typical of those exhibited by a multiplexed holographic sensor.

The term "glucose" as used herein refers to the known cyclic and linear forms of glucose.

The term "ophthalmic device" as used herein refers to contact lenses (both hard and soft), corneal onlays, implantable ophthalmic devices and the like.

The term "contact lens" as used herein refers to any hard or soft lens used on the eye or ocular vicinity for vision correction, diagnosis, sample collection, drug delivery, wound healing, cosmetic appearance or other ophthalmic application. The lens may be a daily-disposable, daily-wear or extended-wear lens.

The term "implantable ophthalmic device" as used herein refers to an ophthalmic device which is used in, on or about the eye or ocular vicinity. Such devices include intraocular lenses, subconjunctival lenses, intracorneal lenses, and shunts/implants (e.g. a stent or glaucoma shunt) that can rest in the cul de sac of an eye.

In a preferred embodiment, the insert is in the form of a contact lens. The lens may be manufactured using any suitable material known in the art. The lens material may be formed by the polymerisation of one or more monomers and optionally one or more prepolymers. The material may comprise a photoinitiator, visibility tinting agent, UV-blocking agent and/or a photosensitiser.

A preferred group of lens materials comprises prepolymers which are water-soluble and/or meltable. It is preferred that such a material comprises one or more prepolymers which are in a substantially pure form (e.g. purified by ultrafiltration). Preferred prepolymers include water-soluble crosslinkable poly(vinyl alcohol) prepolymers (as described in U.S. Pat. Nos. 5,583,163 and 6,303,687); a water-soluble vinyl group-terminated polyurethane, obtainable by reacting an isocyanate-capped polyurethane with an ethylenically unsaturated amine (primary or secondary amine) or an ethylenically unsaturated monohydroxy compound, wherein the isocyanate-capped polyurethane can be a copolymerisation product of at least one polyalkylene glycol, a compound containing at least 2 hydroxyl groups, and at least one compound with two or more isocyanate groups; derivatives of a polyvinyl alcohol, polyethyleneimine or polyvinylamine (see, for example, U.S. Pat. No. 5,849,841); a water-soluble crosslinkable polyurea prepolymer as described in U.S. Pat. No. 6,479,587; crosslinkable polyacrylamide; crosslinkable statistical copolymers of vinyl lactam, MMA and a comonomer, as disclosed in EP-A-0655470 and U.S. Pat. No. 5,712,356; crosslinkable copolymers of vinyl lactam, vinyl acetate and vinyl alcohol, as disclosed in EP-A-0712867 and U.S. Pat. No. 5,665,840; polyether-polyester copolymers with crosslinkable side chains, as disclosed in EP-A-0932635; branched polyalkylene glycol-urethane prepolymers, as disclosed in EP-A-0958315 and U.S. Pat. No. 6,165,408; polyalkylene glycol-tetra(meth)acrylate prepolymers, as disclosed in EP-A-0961941 and U.S. Pat. No. 6,221,303; and crosslinkable polyallylamine gluconolactone prepolymers, as disclosed in WO-A-00/31150.

The lens may comprise a hydrogel material. Typically, hydrogel materials are polymeric materials which are capable of absorbing at least 10% by weight of water when fully hydrated. Hydrogel materials include poly(vinyl alcohol) (PVA), modified PVA (e.g. Nelfilcon A), poly(hydroxyethyl methacrylate), poly(vinyl pyrrolidone), PVA with a poly(carboxylic acid) (e.g. Carbopol), poly(ethylene glycol), polyacrylamide, polymethacrylamide, silicone-containing hydrogels, polyurethane, polyurea, and the like.

Alternatively, the device may be an implantable ophthalmic device. Glucose levels in tears may be much lower than blood glucose levels. With an implantable ophthalmic sensor, one can monitor glucose levels in aqueous humor or interstitial fluid, to where glucose levels can be much higher than glucose levels in tears. Preferably, the device is in the form of a subconjunctive implant, intracorneal lens, stent or glaucoma shunt.

The holographic support medium is one in which a hologram can be made and which is capable of exhibiting one or more of the properties of the sensitive mechanisms described herein. The hologram may be disposed on or in, part of or throughout the bulk of the volume of the support medium. Particularly in the case of a contact lens, the support medium may be an integral part of the device, e.g. the body of a lens may itself comprise or form a holographic support medium.

The support medium preferably comprises a native or modified matrix with viscoelastic properties which alter as a result of an interaction with an analyte species. For example, the matrix may be formed from the copolymerisation of (meth)acrylamide and/or (meth)acrylate-derived comonomers. In particular, the monomer HEMA (hydroxyethyl methacrylate) is readily polymerisable and cross-linkable. PolyHEMA is a versatile support material since it is swellable, hydrophilic and widely biocompatible.

Figure 21A:
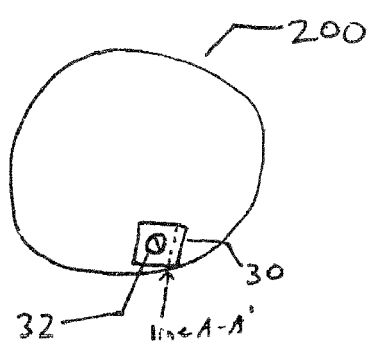
FIG. 21a is a schematic representation of a contact lens comprising a holographic element according to an embodiment of the present invention.
Figure 21B:
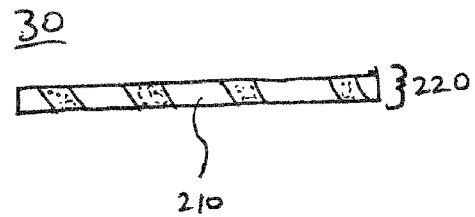

Referring to FIG. 21b, a device in the form of a contact lens 200 is preferably obtained by forming a holographic element 30 (depicted here having an image 32) and then embedding the element into a contact lens. For example, a contact lens sensor may be obtained using the following protocol:

(a) forming a polymeric holographic sensor (e.g. using phenylboronate ligands) on a glass slide or similar surface;

(b) coating a layer of polyvinylalcohol (PVA), preferably "Nelfilcon", onto the surface of the sensor, with subsequent cross-linking of the layer;

(c) extracting any toxic components from the coated sensor (e.g. using 1:1 mixture of methanol:water overnight at 40° C.), followed by autoclaving;

(d) removing the sensor from the slide and cutting from it a disc of about 4 mm diameter; and (e) inserting a disc into a contact lens mould containing a contact lens and PVA, preferably Nelfilcon, then cross-linking and autoclaving the components to form the finished lens.

Referring to FIG. 21b, a holographic sensor 30 of the type used in the invention to generally comprises a medium 210 (which can be, for example, a thin film of polymeric material) and, disposed throughout the volume of the medium 210, a hologram 220. The support medium may interact with an analyte resulting in a variation of a physical property of the medium. This variation induces a change in an optical characteristic of the holographic element, such as its polarisability, reflectance, refractance or absorbance. If any change occurs whilst the hologram is being replayed by incident broad band, non-ionising electromagnetic radiation, then a colour or intensity change, for example, may be observed.

The sensor may be prepared according to the methods disclosed in WO95/26499, WO99/63408 and WO03/087789. The contents of these and other patent specifications identified herein are incorporated herein by reference.

More than one hologram may be supported on, or in, a holographic element. Means may be provided to detect the or each variation in radiation emanating from the or each hologram, arising as a result of a variation in the or each optical characteristic. The holographic elements may be dimensioned and arranged so as to sense two independent events/species and to affect, simultaneously, or otherwise, radiation in two different ways. Holographic elements may be provided in the form of an array.

An illuminating source of non-ionising radiation, for example visible light, may be used to observe variation(s) in the, or each, optical characteristic of the holographic element. The extent of interaction between the holographic medium and the analyte species is reflected in the degree of change of the physical property, which is detected as a variation in an optical characteristic, preferably a shift in wavelength of non-ionising radiation.

The property of the holographic element which varies may be its charge density, volume, shape, density, viscosity, strength, hardness, charge, hydrophobicity, swellability, integrity, cross-link density or any other physical property. Variation of the or each physical property, in turn, causes a variation of an optical characteristic, such as the polarisability, reflectance, refractance or absorbance of the holographic element.

There are a number of basic ways to change a physical property, and thus vary an optical characteristic. The physical property that varies is preferably the volume of the support medium and, in turn, the spacing of the holographic fringes of the holographic element. This variation may be achieved by incorporating specific groups into the support matrix, where these groups undergo a change in, for example, conformation, charge or the degree of cross-linking upon interaction with the analyte, and cause an expansion or contraction of the support medium. An example of such a group is the specific binding conjugate of an analyte species. Another variation is in the active water, solvent or charge content of the support medium. In this case, the holographic support medium is preferably in the form of a gel.

Analyte molecules that can react with at least two functional groups in the element may form a reversible cross-link between separate parts of the support matrix, thereby altering the visco-elastic properties of the support matrix. Consequently, if present within a solvent-containing environment, and the support matrix changes, the support matrix contracts and the separation of the fringes is reduced. Specificity may be provided by ensuring that specific binding sites are provided within the medium.

The support medium may comprise a receptor which is capable of binding or interacting specifically with the analyte. Suitable receptors include antibodies, lectins, hormone receptors, drug receptors, enzymes, aptamers, nucleic acids, nucleic acid analogues, and fragments thereof.

A receptor may be incorporated into a support medium using any suitable method known in the art. For example, a prepolymer and receptor may comprise matching functional groups; the two components can then be covalently linked with one another. Alternatively, a receptor may be incorporated in a vinylic monomer which a component of the lens-forming material.

One parameter determining the response of the system is the extent of cross-linking. The number of cross-linking points due to polymerisation of monomers should not be so great that complex formation between polymer and analyte-binding groups is relatively low, since the polymer film may become too rigid. This may inhibit the swelling of the support medium.

By way of example of a glucose sensor, a hydrogel-based hologram may have a support medium comprising pendant glucose groups and a lectin, preferably concanavalin A (con A). The lectin binds to the pendant glucose groups and acts as a cross-linker in the polymer structure. In the presence of freely diffusible glucose, the extent of cross-linking will decrease as glucose in solution displaces polymer-attached glucose from the binding sites on the lectin, resulting in swelling of the polymer. Volume changes in hydrogel films containing pendant glucose groups and conA can be observed using a reflection hologram. A volume change in the hydrogel alters the fringe separation of the holographic structure and can be followed as a shift in the peak wavelength of the spectral reflected response.

Water-based systems are preferred in such a holographic sensor, since they protect the lectin from exposure to organic solvents. Examples of suitable glucose components are high molecular weight dextran, and the monomers allylglucoside and 2-glucosyloxyethyl methacrylate (GEMA). Dextran, having no inherent polymerisable functionality, can be entrapped during the polymerisation of acrylamide-based monomers; allylglucoside and GEMA can be polymerised either individually or together with comonomers. The polymers are preferably prepared as thin films on glass supports.

A holographic glucose sensor may comprise any suitable glucose receptor, particularly one which allows a reversible change in a physical property of the support medium upon binding with glucose. For example, the support medium may comprise pendant boronic acid groups, such as phenylboronic acid or a derivative thereof. Two adjacent diol groups in glucose bind with a boronic acid group in a reversible condensation reaction. Thus in a holographic element, reaction of glucose with pendant phenylboronic acid groups causes an expansion of the support medium, due to the formation of boronate esters. Without wishing to be bound by theory, it is believed that the boronate esters are negatively charged and effect a Donan potential, causing water to partition into the support medium. This expansion is observed as a shift in the reflectance maxima to longer wavelengths. The sensing ability of boronic acid groups is strongly dependent on the molecular geometry and the aromatic species where the boronic acid group is present. Thus, glucose sensitive probes can be made with a variety of affinities, in the mM range for blood glucose, and in the μM range for tear glucose. Preferred boronic acid groups include those described in WO04/081624.

Boronic acid compounds, in particular phenylboronic acid compounds, are versatile receptors since they may be used for the detection of a variety of carbohydrates. In physiological fluids, this lack of selectivity is not a problem because most sugars are found on glycoproteins and other macromolecular structures, i.e. they are already bound and thus cannot bind to the boronic groups of the support medium. Glucose is the only sugar that is found free in relatively high concentration. Lactate (lactic acid), however, may pose a problem since it is an α-hydroxy acid which binds to to boronic acid groups and is, in ocular fluids, generally present in a greater concentration than glucose.

The problem of lactate interference can be addressed by incorporating, in the device, a group which repels lactate. Lactate carries an overall negative charge in physiological fluids and thus, for example, the support medium may carry a group having a negative charge, the magnitude of which will be apparent to those skilled in the art. An example of such a group is glycolic acid, which can be incorporated into the support medium by the polymerisation of monomers including, for example, acrylamidoglycolic acid. The glycolic acid moiety competes with glucose and lactate for available phenylboronic acid sites however, since the moiety carries a negative charge, it repels lactate but not glucose. Alternatively, the boronic receptor may itself carry a substantial negative charge or polarisation, e.g. by coordinating the boron atom with suitable electron-donating groups. An example of such a boronic acid is 5-fluoro-2-methylacrylamidophenylboronic acid. Another option is to attach negatively charged groups to the phenyl group of a phenylboronate receptor. The surface of the holographic element or the device may be negatively charged, to reduce the effects of lactate interference.

A sensor can also be made more selective for glucose by incorporating pendant amine groups in the support medium. The nitrogen atom of the amine group may form an intramolecular bond with the boron atom, thereby promoting formation of the more reactive tetrahedral conformation about the boron atom.

When a cis-diol-containing species binds a boronic acid, $RB(OH)_2$, an unstable boronate ester results, the ester having a trigonal planar conformation. The boronate ester normally achieves stability by binding an electron-donating group, to form a more stable, tetrahedral geometry. Typically, boronic acids attain this tetrahedral geometry by binding $OH^-$, forming negatively-charged boronate esters. At relatively high pH, the mechanism is believed to be slightly different. It is thought that the boronic acid first binds $OH^-$, to form tetrahedral $RB(OH)_3^-$, which then reacts with the cis-diol. The tetrahedral $RB(OH)_3^-$ reacts more readily with a cis-diol than the trigonal planar boronate ester.

Without wishing to be bound by theory, the inventors believe that the glucose sensor of WO3/087899 "works" because the formation of a negatively-charged phenylboronate ester produces a Donan potential, causing water to partition into the to support medium. Expansion of the medium is then observed as a shift in the reflectance maxima to longer wavelengths. At low pH values, the boronic acid groups may be unable to form negatively-charged phenylboronate esters and, as a result, detection might not possible. This is probably why the glucose sensor of WO03/087899 is only effective over a limited pH range.

There is a class of phenylboronic acid derivatives which allow for the detection of glucose and other cis-diol-containing analytes across a wide range of pH values. Phenylboronic acids can be modified to promote formation of a more reactive tetrahedral conformation.

For example, the phenyl group may comprise one or electron-withdrawing substituents which, by mediating their electronic effects through the phenyl ring, promote formation of $RB(OH)_3^-$. As another example, a substituent may be capable of forming an intramolecular bond with the boron atom, forcing the boronate into a substantially tetrahedral conformation. Judicious selection of substituents allows the responsiveness of the sensor to be optimised with respect to a particular set of detection conditions.

The medium may comprise a polymer comprising a group of formula (i)

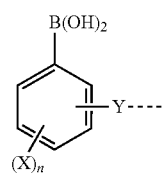

(i)

wherein
n is 0, 1, 2, 3 or 4;
each X (if present) is independently is an atom or group which, via an electronic effect, promotes formation of a tetrahedral geometry about the boron atom; and
Y is a spacer which, when n is 0 or otherwise optionally, is an atom or group which, via an electronic effect, promotes formation of a tetrahedral geometry about the boron atom.

Such a sensor can be used in a method for the detection of an analyte comprising a cis-diol moiety in a fluid, which comprises contacting the fluid with the holographic element and detecting any change of the optical characteristic of the element. The analyte may comprise a plurality of cis-diol moieties; examples of such to analytes include glucose and tartaric acid (tartarate).

The polymeric medium may be obtained by the polymerisation of monomers including a compound of formula (I)

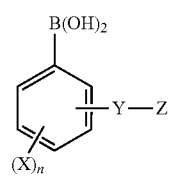

(I)

wherein
X, Y and n are as defined above; and
Z is a polymerisable group.

Another aspect of the invention is a device for the detection of an analyte comprising a cis-diol moiety in a fluid, which comprises a fluid conduit having an inlet, an outlet, and a holographic element as defined above over which the fluid can flow, wherein the device also includes a window whereby non-ionising radiation can irradiate the holographic element. The analyte concentration may change, while the fluid is static. Alternatively, the fluid may be passed continuously over the element.

The variation arises as a result of reaction between the medium and the cis-diol moiety of the analyte, wherein the reaction and the variation are reversible. Since both the reaction and the reverse reaction can occur, analytes such as glucose can be continuously detected, possibly in real time.

The term "alkyl" as used herein refers to a straight or branched chain alkyl moiety having from one to six carbon atoms. The term includes, for example, methyl, ethyl, propyl, isopropyl, butyl, tert-butyl, pentyl, hexyl and the like.

The term "alkoxy" as used herein refers to a straight or branched chain alkoxy moiety having from one to six carbon atoms. The term includes, for example, methoxy, ethoxy, propoxy and the like.

The term "halogen" as used herein refers to fluorine, chlorine, bromine or iodine.

The term "electronic effect" as used herein refers to a direct or indirect effect on the boronic acid group, which promotes formation of a tetrahedral conformation about the boron atom relative to phenylboronic acid. The atom or group may, for example, have an electron-withdrawing, electron-donating, resonance or mesomeric effect on the phenyl ring of formulae (i) and (I) which, in turn, effects the boronic acid group.

The phenyl ring is preferably substituted with one or more electron-withdrawing groups. In this way, formation of RB(OH)$_3^-$ may be promoted. When RB(OH)$_3^-$ reacts with a cis-diol group of glucose, the resulting negatively-charged phenylboronate ester produces a Donan potential, causing water to partition into the support medium. Expansion of the medium is then observed as a shift in the reflectance maxima to longer wavelengths. In general, most sensors of the invention will detect cis-diol-based analytes in this way.

Particularly when the analyte comprises a plurality of cis-diol groups, it is preferred that the phenyl ring is substituted with a group comprising an atom having a lone pair of electrons, which can form an intramolecular (e.g. coordinate) bond with the boron atom, forcing it into a tetrahedral conformation. The boronic acid group may, as a result, be highly reactive. An example of such a group is illustrated below:

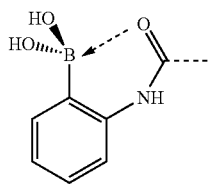

Although such a group is highly reactive to cis-diols, it is thought to form an uncharged phenylboronate ester which, as it is uncharged, cannot produce a Donan potential. Instead, it is believed that, when the analyte comprises a plurality of cis-diol moieties, it can bind two of these highly reactive phenylboronic acid groups and effectively cross-link the support medium. This cross-linking of the support medium causes it to contract, resulting in a shift in the replay wavelength. Examples of analytes which can be detected in this way are glucose and tartarate (tartaric acid).

The interaction between the medium and analyte can be detected remotely, using non-ionising radiation. The extent of interaction is reflected in the degree of change of the physical property, which is detected as a variation in an optical characteristic, preferably a shift in wavelength of non-ionising radiation.

Preferred groups of formula (i) include:

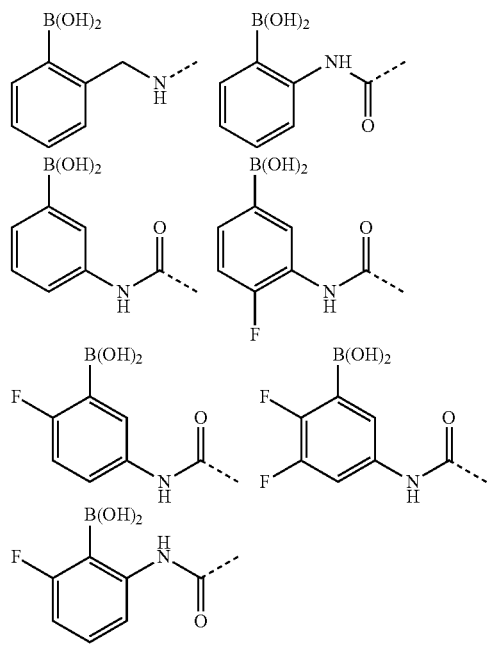

The holographic support medium may be obtained by the polymerisation of monomers, wherein the monomers include a compound of formula (I). Preferred monomers include:

2-(4-(acrylamidomethyl)phenylamino)methyl)phenylboronic acid;
2-((3-methacrylamidopropylamino)methyl)phenylboronic acid;
2-acrylamido-phenylboronic acid;
3-acrylamido-phenylboronic acid; and
3-acrylamido-6-fluoro-phenylboronic acid.

The support medium may comprise one or more macrocyclic groups such as crown ethers, which reversibly bind a range of ionic species. Crown ethers are well known to reversibly bind Group I and Group II metal ions. Therefore a crown ether which is specific to an ionic analyte can be immobilised in the support medium and used to continuously monitor the presence of the analyte.

According to a further aspect of the present invention, the holographic sensor comprises one or more films each containing within its volume a set of two or more holographic recordings, each recording providing a reflected holographic image when the sensor is illuminated by light and where each image is visible to the eye as an indicator that the sensor is showing a response to a predetermined range of concentration of a substance or group of substances to be sensed. More particularly, the presence or appearance of each image is visible to the eye as a function of the response of the sensor to a substance to be sensed; that response may involve the appearance or disappearance, or a change in, a visible image.

Typically, each image in the set of images has a reflection spectrum characterised by its location in the invisible or visible spectrum of light. The location in the spectrum may be unique to each image, such that the images are separable by wavelength-selective means and are therefore wavelength-multiplexed.

A sensor of the invention may be constructed and used in the manner generally described in WO95/26499 or WO99/63408. Thus, for example, the matrix in which the holographic images are formed may be a chemically sensitive polymeric film, or it may comprise a plurality of films that are generally parallel (adjacent or separated by another type of layer). In such an arrangement, each film may provide its own dynamic range, and each film may be designed to detect or measure a specific substance. Each film may present one image or a sub-set of images with its own place in the dynamic range of the sensor; the dynamic range is created by having a plurality of films which provide a plurality or set of images.

More particularly, a sensor of the invention can be in the form of a polymer film or multiple films coated or otherwise disposed onto a transparent or opaque, flexible, semi-rigid or rigid substrate such as glass, plastic, paper or metal. The substrate can be printed, engraved or otherwise marked with a pattern or alpha-numerical markings so as to provide a reference to the holographic images.

The sensor can, alternatively, be provided in or onto a material which is component of or constitutes a device such as contact lens, spectacle lens, optical window into a reaction vessel, instrument display window, domestic window, visual display device or any component where an ambient substance is to be monitored or detected.

The sensor can, alternatively, be provided in or onto a material which is a component of or constitutes an item of clothing so as to confer the ability to monitor or detect ambient substances or physiological substances related to the wearer of the clothing.

The invention can be in the form of multiple layers of holographic polymer films which are interleaved with other types of layers acting as transport media for substances to be detected or monitored or other components of a sample.

Illumination of the hologram(s) by ambient artificial or natural light can be directly onto the plane surfaces or, alternatively, can be provided by illuminating the polymer films along their edges, where the holograms are commonly known as "edge-lit" holograms.

A polymer film which is a sensitive element of the invention may be directly sensitive to an ambient substance or it may be sensitive to the product of a reaction or interaction between the ambient substance and one or more other ambient substances or substances which are provided specifically as components of the holographic sensor assembly. Such a film may be described herein as chemically sensitive, but this is for the purpose of illustration only.

Any of a variety of substances or analytes may be detected by means of the invention, including but not limited to those discussed in the prior art; reference herein to "a substance" includes the use of two or more such substances. Examples of analytes are water, organic liquids, ions, haptens, nucleotides, cells, aldehydes, enzymes, proteins, gases, metabolites, viruses, bacteria, fungi and yeasts. The analyte or a carrier medium may interact with the holographic matrix. In particular examples, the analyte is in liquid, e.g. an enzyme or ethanol in water, or water in an organic solvent.

In a preferred embodiment of the invention, each image from the set of the pictorial images that can be viewed depicts subject matter which is relevant to the sensor application. Each image may depict subject matter which is relevant to the response status indicated by the sensor.

The image may change from one picture to another in relation to the concentration of one or more substances to be detected by the sensor. The change in the pictorial image may be restricted to one or more parts of the image. A change in the pictorial image which is restricted to part of the image may be due to a response to a specific substance to be detected, such that a change in another part of the image is due to a response to another specific substance to be detected. Each part of the image which may be changed may be located anywhere in the three dimensions of the holographic image.

In another preferred embodiment of the invention, the set of images shows a to sequence of numerical information which appears in a sequence corresponding to the concentration of one or more substances detected by the sensor. Preferably, the response of the sensor is calibrated so that the numerical images show numerical quantities which correspond directly with the concentration of a substance detected by the sensor.

In another preferred embodiment of the invention, the set of images shows a sequence of alphabetical information which appears in a sequence corresponding to the concentration of a substance detected by the sensor. Preferably, the alphabetical information is in the form of messages which are relevant to the sensor application. The response of the sensor may be calibrated so that the alphabetical information is in the form of messages which correspond directly with the concentration of a substance detected by the sensor.

In another preferred embodiment of the invention, each image of the set of images comprises an indicating feature which has a specific location, in the space of the image, corresponding to the concentration of a substance detected by the sensor. This is an example of a virtual instrument.

Preferably, the image or indicating feature is a shape. Alternatively, the indicating feature is a picture or is alpha-numerical.

The spatial degree of freedom of the location of the indicating feature may be parallel to the plane of the polymer film. Alternatively, the spatial degree of freedom of the location of the indicating feature is not parallel to the plane of the polymer film but is, instead, in the depth of the image which is an optional characteristic of a holographic image.

Preferably, the location of the indicating feature in either case is marked with reference to a visible scale. The visible scale may be provided as a holographic image provided by a hologram recorded in the same polymer layer as that which provides the indicating feature. Alternatively, the visible scale may be created by a holographic image provided by a different polymer layer from that which provides the indicating feature.

The visible scale may be incorporated with the polymer layer by photographic means. Alternatively, the visible scale may be printed onto the surface of the holographic element, or it may be printed onto a surface which is located adjacent to but separate from the holographic element.

Preferably, the visible scale which is provided as a holographic image is invariant with the concentration of the substance detected by the sensor.

A holographic sensor can provide any combination of pictorial, alphabetical, numerical or spatially-indicating means of displaying the holographic response. Further, an array of holographic sensors may be provided, each providing any combination of the above pictorial, alphabetical, numerical or spatially-indicating means of displaying the holographic response to a multiplicity of substances to be detected or multiplicity of groups of substances to be detected.

Preferably, each element of an array of holographic sensors has a unique response characteristic to the substances to be detected.

The visible display provided by an array of holographic sensors may present an overall pattern which corresponds to the relative concentrations of substances to be detected. The pattern displayed by an array of holographic sensors may be pictorial, numerical or alphabetical. An alphabetical pattern displayed by an array of holographic sensors may represent a message which is relevant to the relative concentrations of substances to be detected.

In any of the above cases, the discrimination of any one visible image from its neighbours in a set of images presented by the holographic sensor can be provided by creating a significant separation in the peak reflected wavelength provided by each image from that of its neighbours.

The discrimination of any one visible image from its neighbours in a sequence of images presented by the holographic sensor may be improved by providing a colour transmission filter located between the light source and a chemically-sensitive polymer film containing the holographic recordings, or between the eye used to view the holographic image and the film, or immediately adjacent to the film but between the film and the eye.

The colour transmission filter may be an integral feature of the material to which a chemically-sensitive polymer film is attached. Alternatively, the colour transmission filter may be an integral feature of the chemically-sensitive polymer film. In any of the above holographic sensors, a colour transmission filter increases the number of multiplexed images for any given dynamic range of response of the sensor, by permitting each image to be closer in peak wavelength to that of its immediate spectral neighbour.

According to a further aspect of the present invention, a method for creating a holographic sensor which has a multiplicity of wavelength-multiplexed images of one or more types chosen from pictorial, numerical, alphabetical, spatially-variant or array types, comprises exposing a polymer film, having already been photosensitised, to a sequence of holographic exposures over the course of a transition of the film from one state of swelling to another.

Each image of the set of images has a characteristic reflection spectrum which may have a peak wavelength which is different from that of other images in the set.

By way of example, the initial state of swelling may be set by placing the polymer film, before exposure, in a solution having a specific pH or ionic strength. Then the polymer film is immersed in a solution with a different specific pH or ionic strength, respectively, so that the film undergoes a transition of swelling or contraction, depending on its response.

Alternatively, the initial state of swelling is set by placing the polymer film, before exposure, in an immediate environment having a specific relative humidity. Then the relative humidity is altered so that the film undergoes a transition of swelling or contraction, depending on its response to relative humidity.

An alternative method for creating a holographic sensor which has a multiplicity of wavelength-multiplexed images of one or more types chosen from pictorial, numerical, alphabetical, spatially-variant or array types is to expose the photosensitive polymer film to each image so that the angle between the object and reference beams used to create the holographic recording is unique to that particular image.

A preferred method for exposing the photosensitive polymer film to a set of images is to expose it to a timed sequence of images of a transmission object where the transmission object is an optical device which is commonly known as a spatial light modulator and is controlled by an electronic signal source, e.g. a computer or a video camera. Preferably, the form of the object represented by the spatial light modulator is chosen from pictorial, numerical, alphabetical, spatially-variant or array types.

Preferably, the image provided by the spatial light modulator is controlled so as to have variable spatial features during the transition of swelling or contraction, so as to provide a means of providing a holographic sensor which has a spatially-variant response to a range of concentrations of a substance to be detected.

The present invention will now be described by way of example only with to reference to the accompanying drawings. These drawings illustrate the changing display of two or more holographic images in response to a substance or group of substances to be detected by a holographic sensor.

In any form of the invention, there exist two or more reflected holographic images, each with a colour characterised by a narrow band spectrum having a peak wavelength. A peak wavelength arises from constructive interference between components of light reflected and diffracted from a periodic structure such as a holographic structure which is composed of a periodic distribution of complex refractive index contained within a thin film of holographic material which is commonly a polymer or similar matrix. In holography, such a periodic distribution of refractive index is commonly known as a distribution of fringes. The peak wavelength is defined mathematically by the Bragg equation which is $$I_{pk}\{x,y,z\}=2\cdot n\{x,y,z\}\cdot L\{x,y,z\}\cdot \cos(q\{x,y,z\})$$

where n is an average index of refraction of the polymer film at a particular location defined generally by the co-ordinates x, y and z in the film, L is the local spacing between adjacent fringes and q is the angle of illumination of light which is incident on the fringes at that location in the film.

FIG. 1 shows a reflected intensity spectrum with a wavelength axis 4 showing three spectral peaks 1, 2 and 3 at one particular state in the dynamic range of the sensor. At this state, the only visible image is that characterised by the peak 2, situated in the region 5 of the spectrum which is normally visible to the eye, bordered by the ultra-violet end of the spectrum 6 and by the infra-red end of the spectrum 7. If the polymer film in which the sensor hologram is made swells during operation of the sensor then the characteristic peak wavelengths of the peaks 1, 2 and 3 all shift to longer wavelengths such that the image characterised by peak 1 originally invisible in the ultra-violet end of the spectrum becomes visible in a new spectral location 8. Similarly, the previously visible image characterised by the spectral peak 2 becomes invisible in the infra-red part of the spectrum, at a spectral location 9. Similarly, a response of the holographic sensor which is a contraction of the polymer film in which the sensor hologram is made is characterised by a shift of the peaks 1, 2 and 3 to shorter wavelengths.

Figure 2:
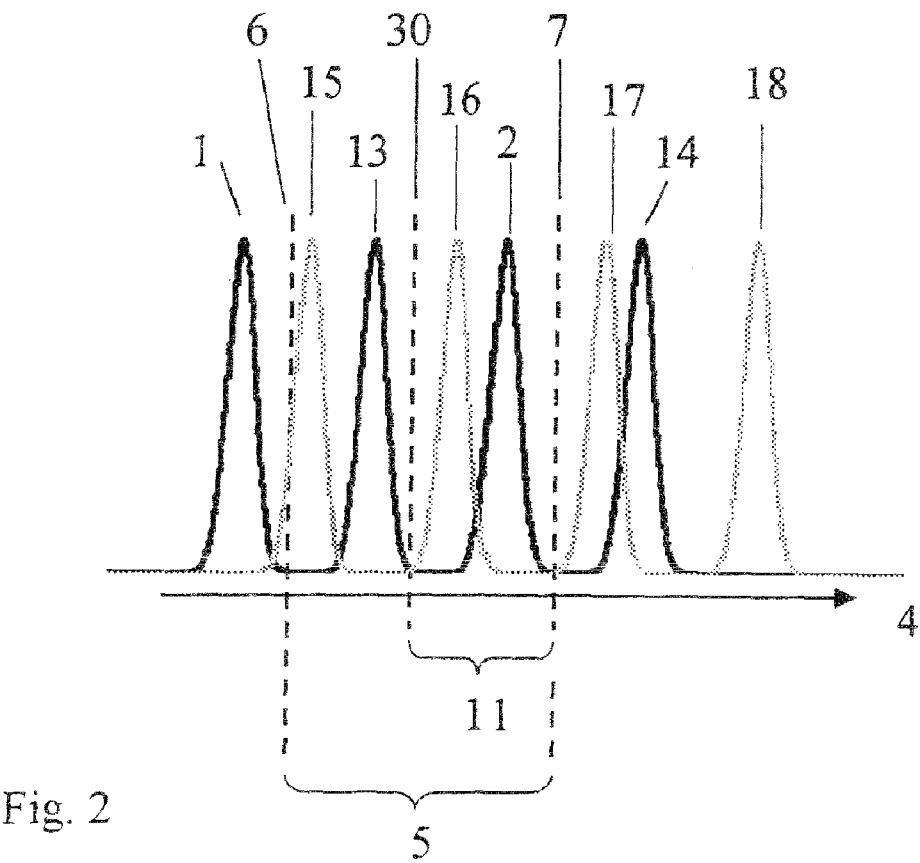
FIG. 2 shows another example of the multiple spectral peaks of a multiplexed reflection hologram typical of those exhibited by a multiplexed holographic sensor.

In an alternative form of the invention, more spectral peaks per region of the spectrum can be provided whilst maintaining discrimination between adjacent images. FIG. 2 shows a restriction of the region 5 of the spectrum which is available to be seen by eye or other detector to a narrower region 11 bounded by a lower end 30 set in this example by a long-wavelength pass filter and an upper end 7 at the upper end of the normally visible part of the spectrum 5. In general, a means of restricting the visible spectrum is not confined to a long wavelength pass edge filter but can be chosen from long wavelength pass filter, short wavelength pass filter, band-pass filter or any other optical device which restricts the detectable part of the whole spectrum. FIG. 2 shows a reflected intensity spectrum with a wavelength axis 4 showing four spectral peaks 1, 2, 13 and 14 at one particular state in the dynamic range of the sensor. At this state, the only visible image is that characterised by the peak 2, situated in the narrower region 11 of the spectrum which is visible to the eye. If the polymer film in which the sensor hologram is made swells during operation of the sensor then the characteristic peak wavelengths of the peaks 1, 2, 13 and 14 all shift to longer wavelengths such that the image characterised by peak 13 originally invisible in the ultra-violet end of the spectrum becomes visible in a new spectral location 16. As the new image characterised by the spectral peak 16 appears the original visible image characterised by the spectral peak 2 becomes invisible as it moves to a new spectral location 17. As further swelling occurs the image characterised by the peak 1 becomes visible in the spectral location 16, or some such similar location in the confined visible region 11. One purpose of providing more spectral peaks per region of the spectrum is to allow a visible change in image to occur in response to a small swelling or contraction of the polymer film in which the holographic images are recorded. Another purpose of providing more spectral peaks per region of the spectrum is to provide a greater number of images throughout the dynamic range of the holographic sensor.

Figure 3A:
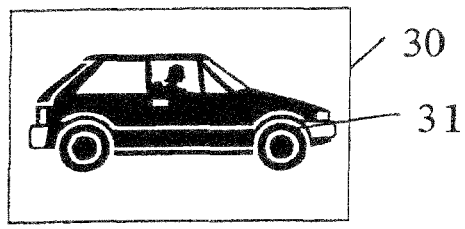
FIGS. 3a and 3b are each schematic drawings of a holographic sensor showing changing pictorial images.
Figure 3B:
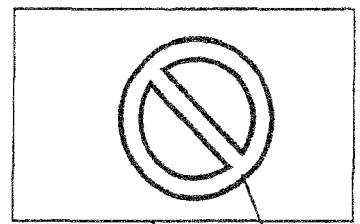

A preferred form of the invention is illustrated in FIG. 3*a* which shows a schematic representing a holographic image 31 of a car provided by a holographic recording in a piece of holographic material 30. In this particular example, the car represents a purpose for which a holographic sensor may be designed, that of detecting the excessive presence of alcohol in the breath of an individual person. One way in which the device represented in FIG. 3*a* may be used is to have a previously invisible image which becomes visible when saturated with moisture from the breath. In another way of using the device, the image such as that illustrated 31, could be always visible if provided in a state of saturation. The detection of excess alcohol in the breath is indicated by the change of the image 31 in FIG. 3*a* to another image 32 in FIG. 3*b* where the image illustrates pictorially that the tested person should not drive. The illustrations are given by way of example only and do not preclude the use of other pictorial images to convey other messages and instructions for the purpose of the use described or for any other application which uses pictorial information to illustrate the relative response of the sensor before and after use.

Figures 4A, 4B, 4C, 4D:
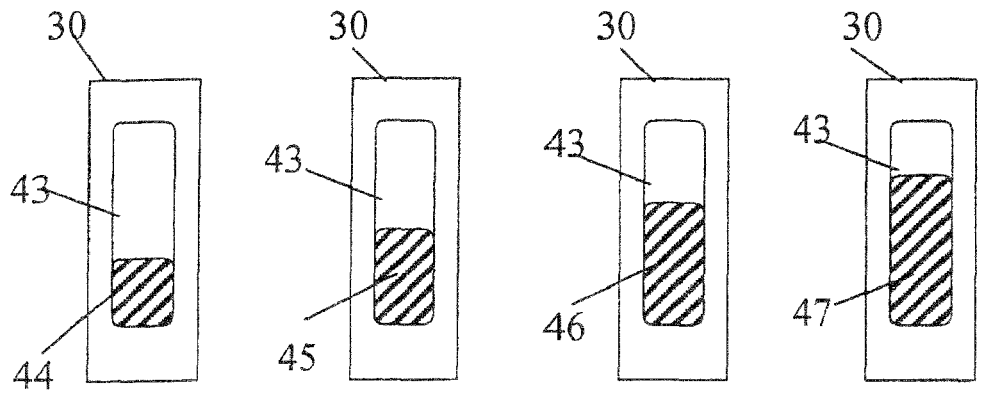
FIGS. 4a to 4d are each schematic drawings of a holographic sensor illustrating a changing image in correspondence with the amount of substance detected.

Another preferred form of the invention is illustrated schematically in FIG. 4*a* which shows a holographic material 30 providing, under illumination, an image of a shape 43 with a part 44 which is differentiated from the scale 43 by having a different appearance by way of colour, shape or pattern. The response of the sensor is indicated by the change in the image segment 44 to that 45 shown in FIG. 4*b*, illustrating an increase in the presence of a substance which is detected by the sensor by occupying a greater part of the image 43. Sequential response to greater amounts of a substance detected is indicated by progressive changes in parts 44 to 47 of the image 43, illustrated in FIGS. 4*a* to 4*d*. In this example, the spatial changes of the image or parts of the image are key features of this preferred form of the invention. An example of a particular application which utilises these essential features of the invention is as a medical diagnostic device which shows an image of a stylised form of the human body where a part of the image appears to be illuminated to indicate a biochemical, metabolic or pathological condition relating to the relevant part of the body.

Figure 5:
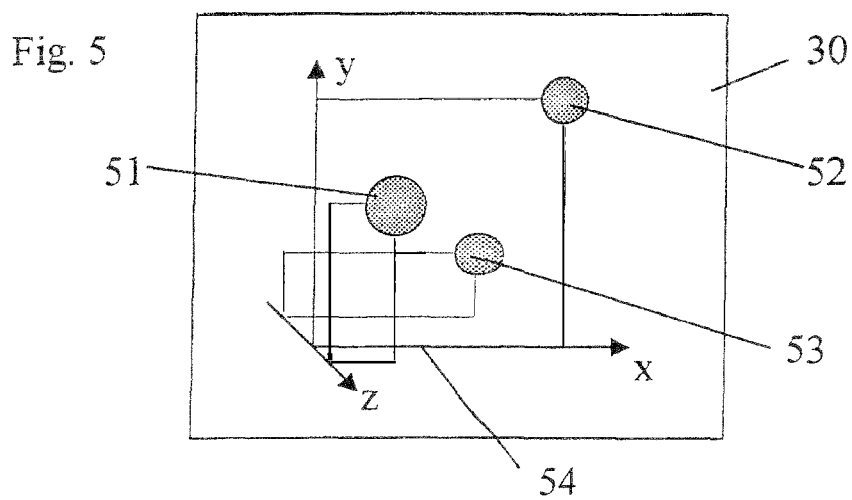
FIG. 5 is a schematic drawing of multiple features of a three-dimensional image.

FIG. 4 illustrates a set of images where features of the images are located in a plane in space. The essential features of the invention are not limited to planar images but can, alternatively, be employed in three-dimensional holographic images. In another preferred form of the invention, the spatial changes of the holographic image or parts of the image are located in the three-dimensional space of the image. FIG. 5 shows a sensor made in a holographic material 30 which provides an image in three dimensions indicated by the axes 54 in x, y and z and having features 51, 52 and 53. The features 51, 52 and 53 can be made to appear or disappear or change in appearance by way of colour, shape or pattern as the visible means of observing the operation of the sensor.

Figures 6A, 6B, 6C, 6D, 6E:
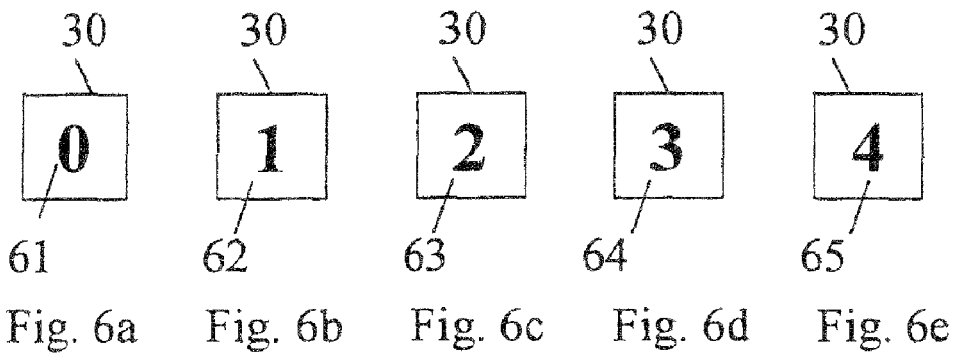
FIGS. 6a to 6e are each schematic representations of a holographic sensor with changing numerical images.
Figures 7A, 7B, 7C, 7D, 7E:
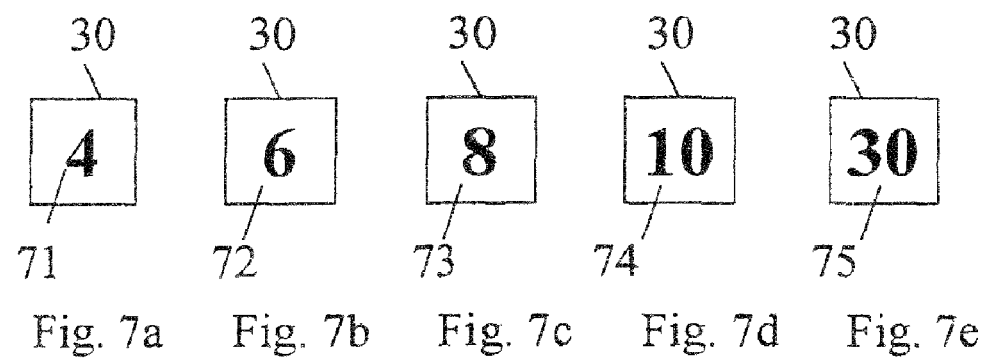
FIGS. 7a to 7e are each schematic representations of a holographic sensor with calibrated numerical images.

In any holographic sensor where an image or part of an image is made to change or become visible or invisible, the image or part of an image can have numerical form, as illustrated schematically in FIG. 6*a*. Numerical images 60-65 shown in FIGS. 6*a* to 6*e* illustrate a response in relation to the concentration of a substance or group of substances to be detected by the sensor. For example, as shown in FIG. 6*a*, a visible image can be provided in the absence of the substance to be sensed (also, as shown in FIGS. 6*b*-6*e*, such an image can be different than a visible image provided in the presence of the substance to be sensed). Alternatively, the numerical response of a holographic sensor can be calibrated to the concentration of a substance or group of substances to be detected, as illustrated in FIGS. 7*a* to 7*e*, by images 71-75.

Figures 8A, 8B, 8C, 8D, 8E:
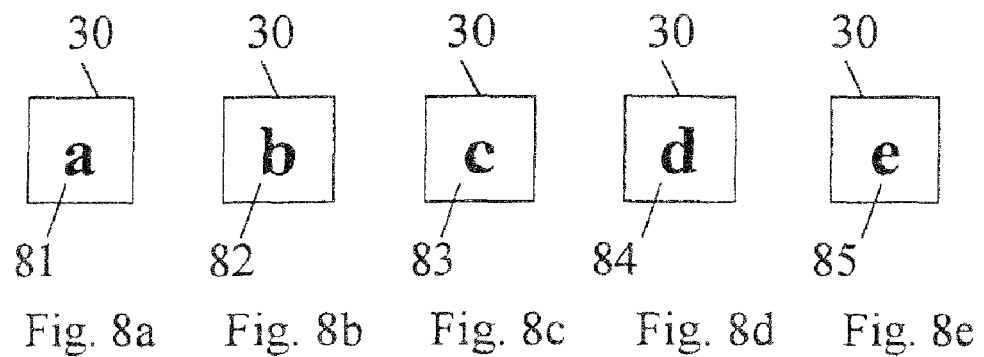
FIGS. 8a to 8e are each schematic representations of a holographic sensor with changing alphabetical images.

In any holographic sensor where an image or part of an image is made to change or become visible or invisible, the image or part of an image can have alphabetical form, as illustrated schematically in FIG. 8*a*. Alphabetical images 81-85 shown in FIGS. 8*a* to 8*e* illustrate a response in relation to the concentration of a substance or group of substances to be detected by the sensor.

In any holographic sensor, the images can optionally show a combination of numerical or alphabetical information relating to the application for which the sensor is intended.

In any holographic sensor which presents alphabetical information, the message which is provided can be related to the application for which the sensor is intended. An example of a holographic sensor for breath alcohol is illustrated in the schematic of FIG. 9*a* which shows a message 91 indicating that the measured level is within bounds accepted by predetermined rules. The schematic of FIG. 9*b* illustrates an example of a message 92 which indicates that the measured level falls outside bounds accepted by predetermined rules.

In any holographic sensor which provides alphabetical information, the message which is provided can be related to the concentration of substance or group of substances to be measured. FIG. 10*a* shows an alphabetical image 101 which indicates a low detected level of substance or group of substances. FIGS. 10*b* and 10*c* indicate, respectively, normal and high levels, by images 102 and 103. Alternatively, the messages provided can be an indicator as to the course of action to be followed as a consequence of carrying out the test provided by the holographic sensor.

The presentation of simple messages in the fashion provided by holographic sensor devices provides an unambiguous and easily understood result and is particularly to suitable for rapid tests or use by unskilled people in a variety of healthcare, consumer or clinical applications though other applications areas are included.

In another preferred form of the invention, illustrated schematically in FIG. 11, each of the multiplexed holographic images is in the form of a pointing indicator. A series of such indicators is multiplexed according to methods described above such that, preferably, only one is visible at any one response state of the sensor. In the example shown in FIG. 11, just two of the indicator images 112 and 113 are shown, though a series of images separated spatially along the direction 114 provides a sequence related to the concentration of a substance or group of substances to be quantified. The pointing indicators 112 and 114 and others not shown in the diagram refer to a scale 111 which can be pictorial or numerical. A numerical scale 111 provides a means of quantifying the response of the sensor. The scale 111 can be chosen from the following types: printed adjacent to the holographic material, printed onto the holographic material, printed on a separate material under the holographic material, photographically created separate to the holographic material, photographically created within the holographic material, holographically created within the holographic material, holographically created in a separate holographic material from that which serves as the sensor material, though the list is not exclusive.

In another preferred form of the invention, illustrated schematically in FIG. 12, each of the multiplexed images is in the form of a pointing indicator which appear to be arranged in three dimensions, out of the plane of the holographic material 30. The characteristic depth which is optionally provided by holographic images is utilised in this form of holographic sensor. A series of such indicators is multiplexed according to methods described above such that, preferably, only one is visible at any one response state of the sensor. In the example shown in FIG. 12, just two of the indicator images 122 and 123 are shown, though a series of images separated spatially along the direction 124 in three spatial dimensions provides a sequence related to the concentration of a substance or group of substances to be quantified. The pointing indicators 122 and 124 and others (not shown) refer to a scale 121 which can be pictorial or numerical. A numerical scale 121 provides a means of quantifying the response of the sensor. The scale 121 is preferably itself a holographic image which is aligned with the sequence of multiplexed pointing indicator images though it can be chosen from the following types: printed onto the holographic material, printed on a separate material under the holographic material, photographically created separate to the holographic material, photographically created within the holographic material, holographically created within the holographic material, holographically created in a separate holographic material from that which serves as the sensor material, though the list is not exclusive. Some benefits of using three-dimensional holographic images in a holographic sensor are that the area of the holographic material can be reduced, allowing test sample volumes to be reduced, manufacturing cost to be reduced and space to be saved.

A preferred method for constructing the multiplexed images for the purpose of providing a holographic sensor is to use a two-beam image-hologram process such as that illustrated by way of example in the schematic of FIG. 13. A laser beam 131 is split into two beams 132 and 133 by a beam-splitter 134. One of the beams 132 is directed by a mirror 135 onto a transparent object 136 via an optional light diffuser 140. Preferably, the transparent object 136 is a spatial light modulator which is a video display device which provides an image under computer control. Alternatively, the transparent object 136 can be a photographic transparency. A benefit of using a computer-controlled spatial light modulator is that the transparent objects it provides as images to be recorded holographically can be rapidly changed in order to create the sequence of holographic images. The illuminated transparent object 136 is located at the object plane of an imaging system 137 which is a set of one or more lenses which provides an image of the object 136 at an image plane where a holographic recording material 138 is situated. The second laser beam 133 is directed, in this example, by a mirror 139 onto the holographic recording material 138 and thus acts as a reference beam (in holographic terminology). The image and the reference beams combine to produce an interference pattern in the holographic recording material 138 in such a way as to allow it to be retained by the material. Two examples of methods of recording a holographic interference pattern are by further chemical processing, if a silver-based recording material, or by using a photo-polymer material and appropriate laser wavelength. An essential feature of this aspect of the invention is that the state of swelling of the holographic recording material 138 is controllable by some means chosen from pH, ion concentration, humidity, water activity or any other means of altering the thickness of the holographic recording material. At each state of swelling of the material a different holographic image is created by the means described until a complete set has to been recorded as a set of multiplexed images which display the response of a holographic sensor in the formats described above.

The following Examples illustrate the invention.

EXAMPLE 1

A contact lens was produced according to the protocol described above. The embedded holographic element comprised 12% mol of 3-acrylamidophenylboronic acid, the synthesis of which is described in WO04/081624.

The lens was placed into the eye of a human volunteer, who then ingested a 44 g bolus of glucose. The response of the contact lens sensor was measured in terms of the shift in the wavelength of reflection. Blood glucose levels were also monitored directly using a conventional glucose sensor.

Figure 14:
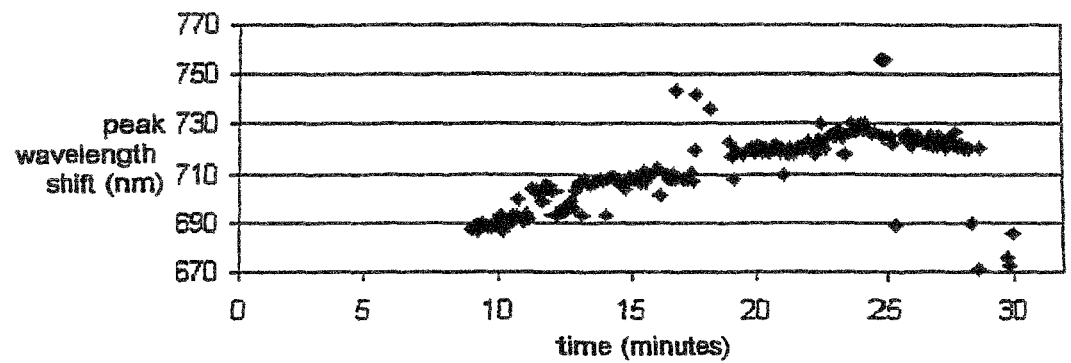
FIGS. 14 and 16 are each graphs of peak wavelength shift against time.
Figure 15:
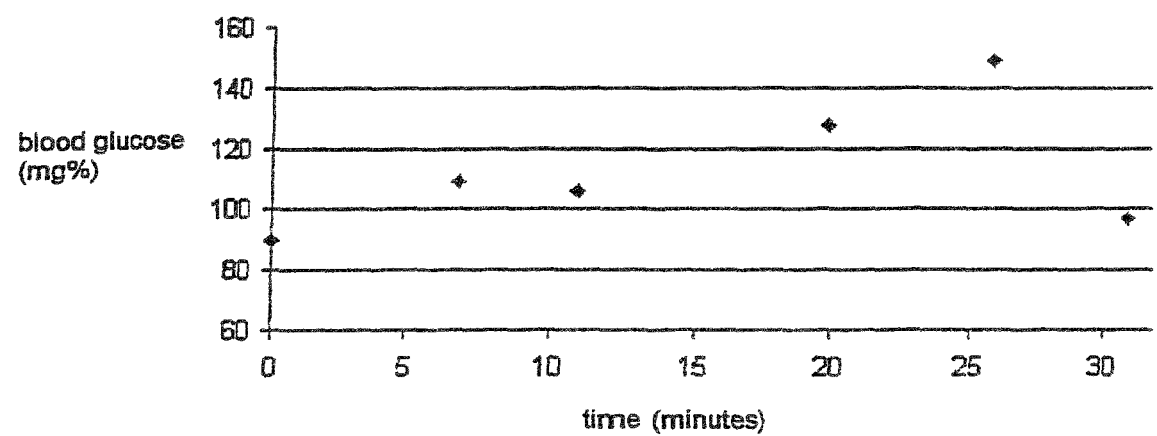
FIGS. 15 and 17 are each graphs of peak blood glucose against time.

FIG. 14 shows the response of the contact lens sensor, and FIG. 15 that of the blood glucose sensor. It is evident that the responses of the two sensors are similar, the peak level of glucose being absorbed at around t=25 minutes.

EXAMPLE 2

An experiment similar to that of Example 1 was performed, using an ophthalmic implant comprising the sensor. The support medium was coated with Nelfilcon (Cibavision).

The experiment was conducted on a rabbit, instead of a human volunteer, the device implanted subcutaneously just below the eye. The rabbit was then anaesthetised using an xylazine-based protocol which causes blood levels of glucose to rise to a level commonly seen in diabetic patients (see Cameron et al, Diabetes Technology & Therapeutics, 2001, 3, 201-207). The concentration of glucose was then monitored using the implant. Again, blood levels of glucose were also monitored directly.

Figure 16:
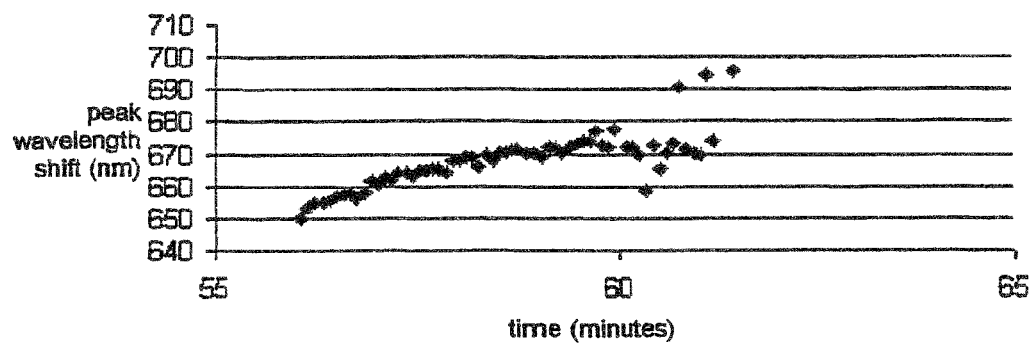
Figure 17:
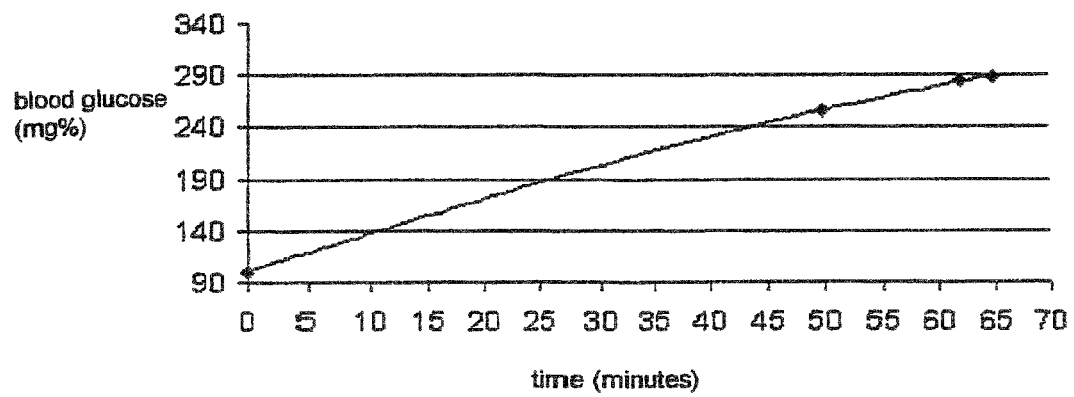

FIG. 16 shows the response of the holographic implant, and FIG. 17 that of the blood glucose sensor. As in Example 1, the responses of the two sensors are similar.

EXAMPLE 3

A holographic support medium was formed by copolymerising 13 mol % 5-fluoro-2-methylacrylamidophenylboronic acid (synthesised according to WO04/081624) and 3% MBA in acrylamide. A holographic image was then recorded in the resulting medium and the sensor used to detect glucose in PBS at pH 7.4 and a temperature of 30° C. A similar experiment was performed to test the sensor's response to lactate.

Figure 18:
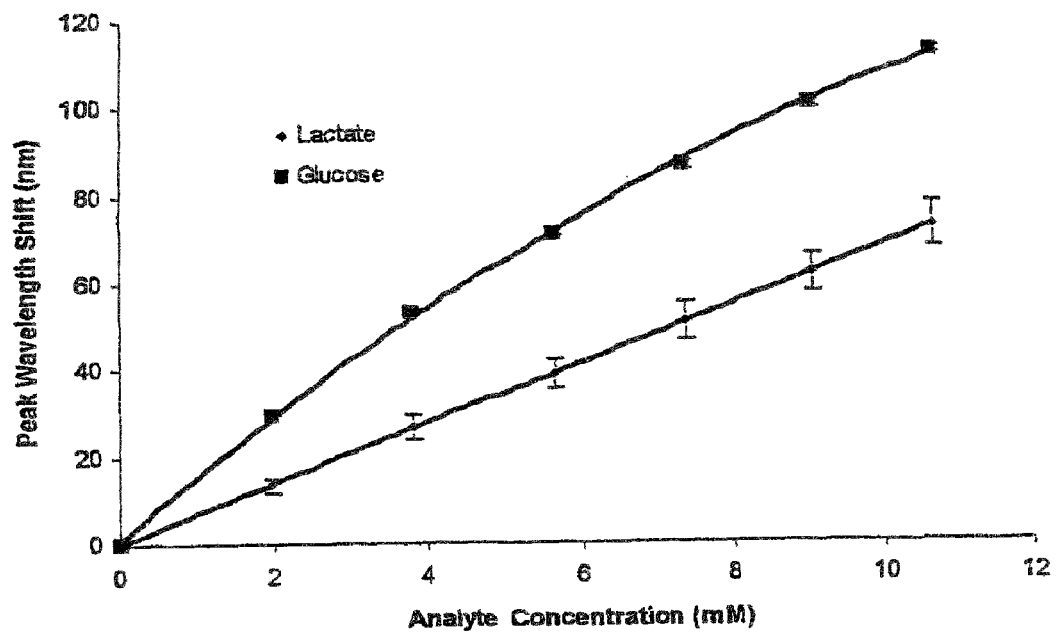
FIGS. 18 to 20 are each graphs of peak wavelength shift against analyte concentration.

The results are shown in FIG. 18. The improved selectivity to glucose over lactate is attributable to the oxygen- and nitrogen-based electron-donating groups coordinated to the boron atom of the phenylboronate receptor. These groups increase the negative change around the boron atom.

EXAMPLE 4

A medium was obtained by polymerising 12 mol % 3-acrylamidophenylboronic acid, 12 mol % acrylamidoglycolic acid and 76 mol % acrylamide, using 2% (w/v) of 2-dimethoxy-2-phenyl-acetophenone (a free radical initiator) in dimethyl sulphoxide. A hologram was recorded in the medium, and the resulting sensor tested for its response to glucose and lactate.

Figure 19:
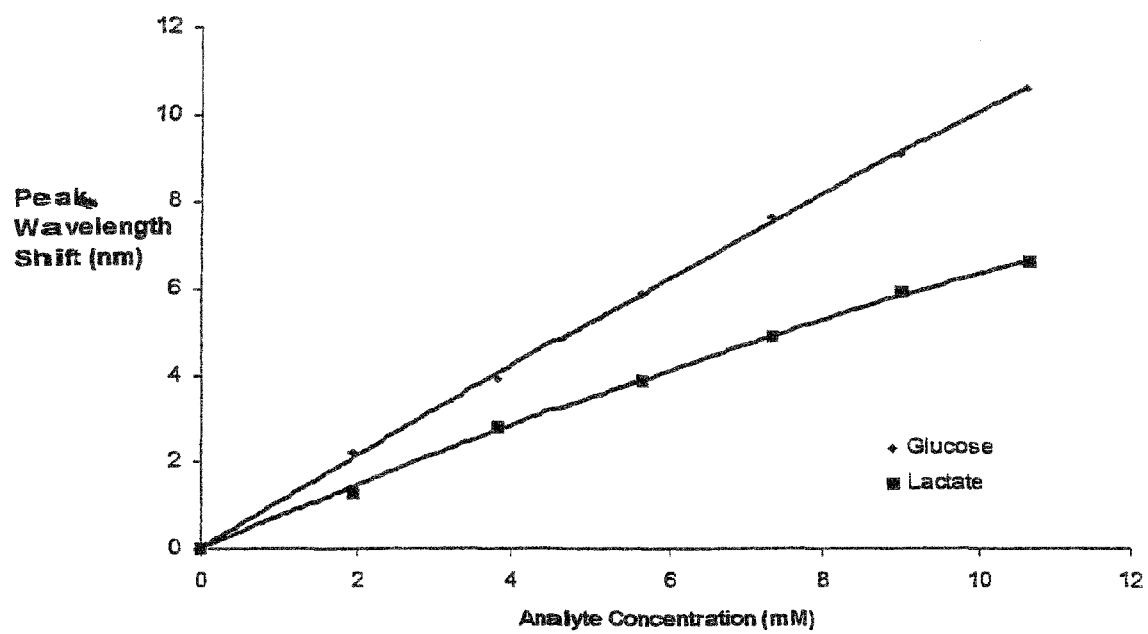

The results are shown in FIG. 19. The presence of acrylamidoglycolic acid reduced the response of the sensor to the two analytes, as the negative charge of the acidic moiety causes a significant degree of swelling of the polymeric medium. However, the sensor was more responsive to glucose than lactate, because the glycolic acid component carries a negative charge which repels lactate, without significantly affecting glucose binding.

EXAMPLE 5

A support medium was formed by copolymerising 11.9 mol % 3-acrylamidophenylboronic acid, 9.2 mol % N-[3-(dimethylamino)propyl]acrylamide, 2.9 mol % methylenebisacrylamide and 76 mol % acrylamide, by exposure to UV light for 1 hour. Silver ions, present in an acetic acid solution, were diffused into the medium, the acidic solution present to prevent "fogging" of the silver by the amine component. A hologram was recorded in the medium, and the resulting sensor tested for its response to glucose and lactate.

Figure 20:
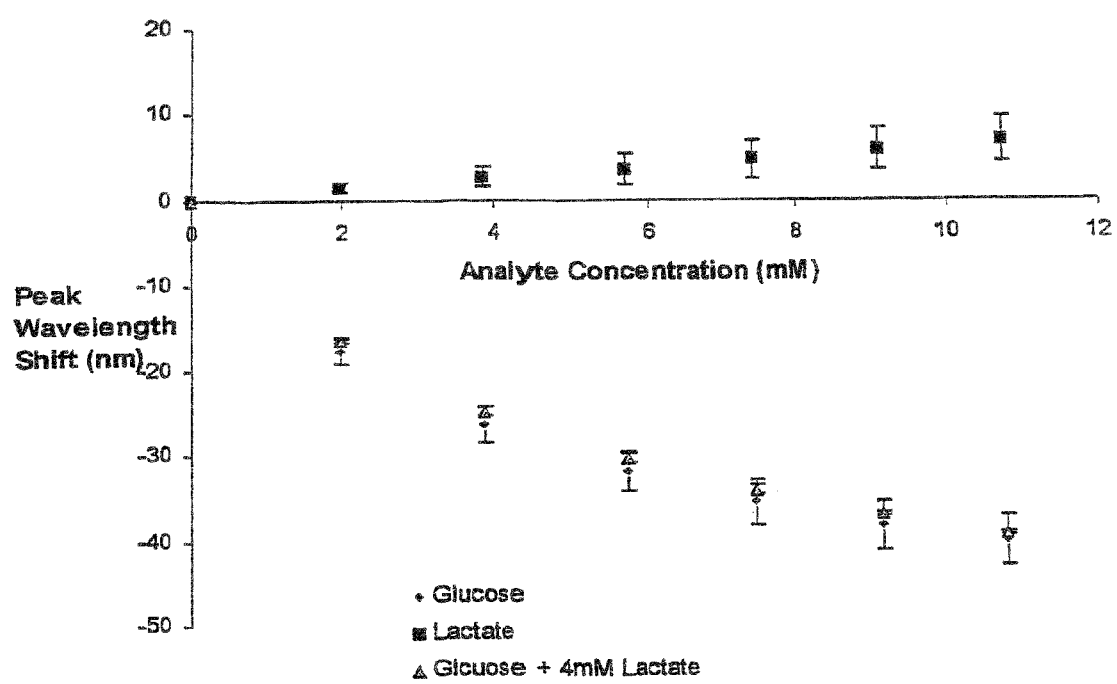

The results are shown in FIG. 20. The sensor was selective for glucose over lactate; the peak wavelength shift for lactate was only about 12% of that for glucose at the same concentration. Also, the wavelength shift is a negative shift for glucose, whereas the binding of lactate effects a positive shift. The presence of "background" (4 mM) lactate had a negligible effect on the sensor's response to glucose.

EXAMPLE 6

3-Acrylamido-phenylboronic acid ("3-APB") was synthesised by reacting 3-amino phenylboronic acid with an excess of acryloyl chloride in an aqueous alkaline solution. The product was extracted in acetone and dried using a rotary evaporator. The structure of 3-APB was confirmed using NMR. The purity was about 90%, TLC showing very little contamination.

3-APB was then copolymerised with acrylamide and N,N'-methylene bisacrylamide, and a hologram recorded within the polymer material. The response to glucose was then tested by increasing the glucose concentration in phosphate-buffered saline (PBS) solution at pH 7.4 in 0.5 mM steps.

The reaction with glucose was fully reversible after the system was flushed twice with fresh buffer. The sensor was also sensitive enough to pick up concentrations of glucose as low as 0.5 mM (9 mg %) with a shift of about 6 nm. This result was highly reproducible with errors of about 5%, even when using a different hologram and instrumentation. Calibration was approximately linear below 2 mM (36 mg %) glucose.

A control was also run where 2 mM KCl was added to the system containing the hologram in PBS pH 7.4 instead of glucose. This was to test the tolerance of the hologram to changes in osmolarity; an increase in osmolarity could lead to a contraction of the polymer. Addition of the salt had no significant effect on the hologram, showing that it could easily tolerate small changes in salt concentration.

EXAMPLE 7

3-APB, the synthesis of which is described in Example 6, was recrystallised from an aqueous ethanolic solution with a purity of about 98%; both NMR and TLC showed that there were no contaminants present.

3-APB was co-polymerised with acrylamide and N,N'-methylene bisacrylamide to form a polymer comprising about 15 mole % of purified 3-APB and about 1.55 mole % N,N'-methylene bisacrylamide (cross-linker). A hologram was then recorded in the polymer.

In a calibration curve for response to glucose in PBS pH 7.4 at 30° C., the purified 3-APB had a response of about 14 nm per millimolar glucose whereas the 90% pure 3-APB of Example 6 had a response of only 11 nm per millimolar glucose for a hologram with the same mole % of 3-APB.

A polymer comprising a 3-APB molar fraction of 25% was synthesised using the same amount of cross-linker (1.55 mole %) and the same amount of solids per unit is volume of solvent. A hologram was recorded within the polymer and then calibrated.

The increased amount of 3-APB increased the sensitivity of the hologram for glucose by over 70%. This allowed small changes in glucose concentration to be accurately detected.

EXAMPLE 8

2-Acrylamido-phenylboronic acid ("2-APB") was synthesised by reacting 2-aminophenylboronic acid with an excess of acryloyl chloride in an aqueous alkaline solution. The product was extracted in acetone and dried using a rotary evaporator. The structure of 2-APB was confirmed using NMR. The purity was shown to be greater than 90%.

2-APB was then copolymerised with acrylamide and N,N'-methylene bisacrylamide to form a co-polymer with 20% 2-APB and 1.5% N,N'-methylene bisacrylamide (cross-linker). A hologram was then recorded within the polymeric medium. The resulting holographic sensor was then tested for its response to glycerol, ethylene glycol, lactate, tartaric acid and glucose. Testing was conducted using PBS (pH 7.4) at 30° C.

The response of the sensor to the five analytes showed that the sensor is unresponsive to changes in glycerol, ethylene glycol and lactate concentration. The sensor is, however, sensitive to change in the levels of tartaric acid and glucose; this was observed as a blue shift in the peak diffraction wavelength, indicating that the support medium contracted in the presence of these analytes.

This selectivity to tartaric acid and glucose is believed to be attributable to the fact that both these analytes contain two cis-diol groups; the other analytes tested contain only one. Thus, tartaric acid and glucose can bind two 2-APB groups and, effectively, cross-link the holographic support medium, causing it to contract.

The response to tartaric acid is greater than for glucose because the two cis-diol sites of tartarate are identical and thus of equal affinity for 2-APB. The cis-diol sites of glucose are slightly different. If such a sensor were to be used to monitor physiological levels of glucose, then the greater response to tartaric acid would not be a problem since the latter is not found free in solution in the body.

We claim:

1. An ophthalmic device which comprises a holographic element comprising a medium comprising a phenylboronic acid group and, disposed therein, a reflection hologram, wherein an optical characteristic of the element changes as a result of a variation of a physical property of the medium, wherein the variation arises as a result of interaction between the medium and an analyte present in an ocular fluid, and wherein an image of the reflection hologram is responsive to invisible radiation.

2. The device according to claim 1, wherein the medium consists essentially of a polymer comprising the phenylboronic acid group.

3. The device according to claim 2, wherein the medium consists of the polymer comprising the phenylboronic acid group.

4. The device according to claim 1, wherein the phenylboronic acid group is selected from the group consisting of:

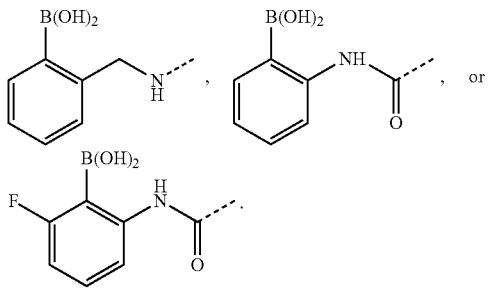

5. The device according to claim 1, wherein the phenylboronic acid group is selected from the group consisting of:

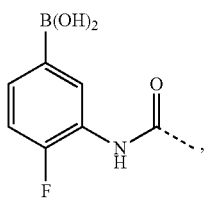

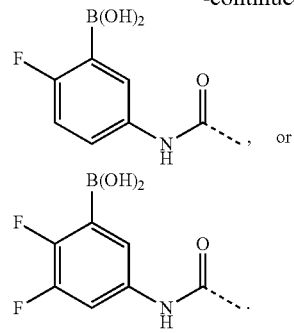

6. The device according to claim 1, wherein the holographic element does not contain silver.

7. The device according to claim 1, wherein the interaction is a reversible chemical reaction.

8. The device according to claim 1, wherein the analyte is glucose.

9. The device according to claim 1, wherein the medium is a polymer of monomers including acrylamide.

10. The device according to claim 1, wherein the medium is a polymer of monomers including 3-acrylamidophenylboronic acid.

11. The device according to claim 10, wherein the medium comprises a group which is capable of repelling lactate, the group comprising a substantial negative charge.

12. The device according to claim 10, wherein the medium comprises an amine group.

13. The device according to claim 1, wherein the ophthalmic device is a contact lens.

* * * * *